US012636426B2

(12) United States Patent
Ryan

(10) Patent No.: US 12,636,426 B2
(45) Date of Patent: May 26, 2026

(54) HONEYCOMB CELL PACKAGING

(71) Applicant: Becton, Dickinson and Company, Franklin Lakes, NJ (US)

(72) Inventor: Kevin M. Ryan, Whitehouse Station, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 17 days.

(21) Appl. No.: 18/730,816

(22) PCT Filed: Jan. 26, 2023

(86) PCT No.: PCT/US2023/061349
§ 371 (c)(1),
(2) Date: Jul. 22, 2024

(87) PCT Pub. No.: WO2023/147407
PCT Pub. Date: Aug. 3, 2023

(65) Prior Publication Data
US 2025/0114514 A1     Apr. 10, 2025

Related U.S. Application Data

(60) Provisional application No. 63/304,203, filed on Jan. 28, 2022.

(51) Int. Cl.
*A61M 5/00* (2006.01)
*B65D 25/10* (2006.01)

(52) U.S. Cl.
CPC ........... *A61M 5/002* (2013.01); *B65D 25/108* (2013.01)

(58) Field of Classification Search
CPC ..... A61M 5/002; B65D 25/108; B65D 25/10; A61J 1/16
USPC ......................... 206/366, 365, 370, 563, 562
See application file for complete search history.

(56) References Cited

U.S. PATENT DOCUMENTS

| | | | | |
|---|---|---|---|---|
| 8,485,357 | B2 * | 7/2013 | Song | B01L 9/00 |
| | | | | 211/74 |
| 9,139,350 | B2 * | 9/2015 | Yeager | B65D 85/70 |
| 9,718,583 | B2 * | 8/2017 | Nicoletti | B65D 65/02 |
| D835,805 | S * | 12/2018 | Evans | D24/229 |
| 10,227,161 | B2 * | 3/2019 | Auerbach | A61M 5/008 |
| 2007/0151882 | A1 * | 7/2007 | Cocheteux | A61M 5/008 |
| | | | | 206/364 |
| 2012/0080341 | A1 * | 4/2012 | Finke | A61M 5/002 |
| | | | | 206/366 |
| 2015/0183541 | A1 * | 7/2015 | Deutschle | A61L 2/208 |
| | | | | 206/439 |
| 2018/0126066 | A1 | 5/2018 | Narvekar et al. | |
| 2019/0070357 | A1 | 3/2019 | Evans et al. | |
| 2019/0083697 | A1 | 3/2019 | Evans et al. | |

(Continued)

*Primary Examiner* — Steven A. Reynolds
(74) *Attorney, Agent, or Firm* — The Webb Law Firm

(57) ABSTRACT

Packaging for medical consumables includes a plurality of cells arranged in a lattice, each of the cells comprising a sidewall having a plurality of walls, and a top barrier film covering open ends of the plurality of cells to maintain a sterile environment within the plurality of cells. The sidewalls and the top barrier film are shaped so as to constrain a consumable contained within each of the plurality of cells to zero degrees of freedom. At least one of the plurality of walls of each cell is shared with a bordering cell. The sidewall of each cell defines a gap for insertion of an end effector of a robotic arm.

19 Claims, 5 Drawing Sheets

(56)                References Cited

U.S. PATENT DOCUMENTS

2020/0253824 A1 * 8/2020 Maritan ................... A61J 1/16
2021/0031980 A1 * 2/2021 Kloke ..................... B65D 1/34

* cited by examiner

HONEYCOMB CELL PACKAGING

CROSS-REFERENCE TO RELATED APPLICATIONS

This application is the United States national phase of International Application No. PCT/US23/61349 filed Jan. 26, 2023, and claims priority to U.S. Provisional Application Ser. No. 63/304,203, entitled "Honeycomb Cell Packaging", filed Jan. 28, 2022, the disclosures of which are hereby incorporated by reference in their entireties.

BACKGROUND OF THE INVENTION

Field of the Invention

The present disclosure relates to packaging, and more particularly to packaging for medical consumables handled by robots.

Description of Related Art

Robotics have become ubiquitous in the field of medication device preparation and handling for processes such as drug compounding, syringe filling, and device disinfecting. Many of the robotic devices presently on the market require manual loading of consumables, such as syringes, vials, and the like onto a rack for access by the robot. Manual loading introduces human touch contamination to the consumables, as well as increasing loading time. Attempts to automate loading, for example by having the robotic devices load themselves, have been largely thwarted by conventional medical consumable packaging. In particular, conventional medical consumable packaging is designed to facilitate human unpacking, and often is difficult for robotic handling due to random orientation of the consumables and deformability of the packaging.

Conventional medical consumable packaging may have three parts. Immediately adjacent the consumables is a primary packaging, such as a loose bag or blister-packed pouch. The primary packaging is contained in secondary packaging, such as a cardboard or thermoformed tub, which may include a tuck lid. The primary packaging is typically loosely stacked or randomly oriented in the secondary packaging. The secondary packaging is itself contained in tertiary packaging, such as a cardboard case box. The relative ease of deformability of the primary packaging presents both hardware and software challenges in designing robotic devices that can reliably remove the consumables from the primary packaging. Similarly, the loose and/or random distribution of the primary packaging within the secondary packaging requires robotic devices to navigate several degrees of freedom to reliably remove the primary packaging from the secondary packaging, again necessitating complex hardware and software.

In view of the above challenges, robotic medication preparation devices are typically designed under the premise that a human will perform unpacking of the consumables and load the consumables into a suitable location and orientation for access by the robotic devices. An example of such a robotic medication preparation device is illustrated in FIG. 5. A robotic arm 10 includes an end effector 12, e.g. a robotic gripper finger, for grasping syringes 30. The syringes 30 are arranged on a rack 20 in a uniform orientation such that the end effector 12 can reliably grasp and manipulate the syringes 30. Due to the aforementioned deficiencies in conventional packaging, the syringes 30 are manually removed from their packaging and placed in the rack 20 by a technician. As noted above, this manual loading of the rack 20 requires significant man-hours and introduces touch contamination to the processing of the syringes 30.

SUMMARY OF THE INVENTION

Embodiments of the present disclosure are directed to packaging for medical consumables, although the packaging disclosed herein could also be used in other fields.

In some embodiments, packaging for medical consumables includes a plurality of cells arranged in a lattice, each of the cells comprising a sidewall having a plurality of walls, a top barrier film covering open ends of the plurality of cells to maintain a sterile environment within the plurality of cells. The sidewalls and the top barrier film are shaped so as to constrain a consumable contained within each of the plurality of cells to zero degrees of freedom. At least one of the plurality of walls of each cell is shared with a bordering cell. The sidewall of each cell defines a gap for insertion of an end effector of a robotic arm.

In some embodiments, the top barrier film includes a plurality of perforations corresponding to the plurality of cells.

In some embodiments, each of the plurality of perforations is offset from a perimeter of the corresponding cell toward a center of the corresponding cell.

In some embodiments, the plurality of cells are arranged in a plurality of rows, and the cells in one of the plurality of rows are offset by one half cell width relative to the cells of a preceding row of the plurality of rows.

In some embodiments, each cell has a hexagonal cross-sectional profile.

In some embodiments, the plurality of walls includes six walls. The length of a first wall and a fourth wall of the plurality of walls are the same length. The length of a second wall, a third wall, a fifth wall, and a sixth wall of the plurality of walls are the same length.

In some embodiments, the second wall and the third wall of the plurality of walls are a mirror image of the fifth wall and the sixth wall of the plurality of walls.

In some embodiments, the packaging further includes a bottom barrier film covering base ends of the plurality of cells to maintain a sterile environment within the plurality of cells.

Other embodiments of the present disclosure are directed to a system including a plurality of medical consumables and packaging for the medical consumables. The packaging includes a plurality of cells arranged in a lattice, each of the cells comprising a sidewall having a plurality of walls, and a top barrier film covering open ends of the plurality of cells to maintain a sterile environment within the plurality of cells. Each of the plurality of consumables is disposed in one of the plurality of cells. The sidewalls and the top barrier film are shaped so as to constrain the consumable contained within each of the plurality of cells to zero degrees of freedom. At least one of the plurality of walls of each cell is shared with a bordering cell. The sidewall of each cell defines a gap for insertion of an end effector of a robotic arm between the sidewall and the consumable disposed in each cell.

In some embodiments, each of the plurality of consumables is disposed in the packaging in the same orientation.

In some embodiments, the plurality of consumables includes a plurality of syringes.

In some embodiments, the plurality of the syringes are disposed in the packaging such that a needle of each syringe extends toward a base of the packaging and a plunger of each syringe extends toward a top of the packaging.

In some embodiments, the sidewall defines at least one contact point with the consumable disposed in the cell.

In some embodiments, the sidewall defines at least one contact point with a flange of the syringe disposed in the cell.

In some embodiments, the top barrier film includes a plurality of perforations corresponding to the plurality of cells.

In some embodiments, each of the plurality of perforation is offset from a perimeter of the corresponding cell toward a center of the corresponding cell.

In some embodiments, the plurality of cells are arranged in a plurality of rows, and the cells in one of the plurality of rows are offset by one half cell width relative to the cells of a preceding row of the plurality of rows.

In some embodiments, each cell has a hexagonal cross-sectional profile.

In some embodiments, the plurality of walls includes six walls. The length of a first wall and a fourth wall of the plurality of walls are the same length. The length of a second wall, a third wall, a fifth wall, and a sixth wall of the plurality of walls are the same length.

In some embodiments, the second wall and the third wall of the plurality of walls are a mirror image of the fifth wall and the sixth wall of the plurality of walls.

Further details and advantages of the various examples described in detail herein will become clear upon reviewing the following detailed description of the various examples in conjunction with the accompanying drawing figures.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
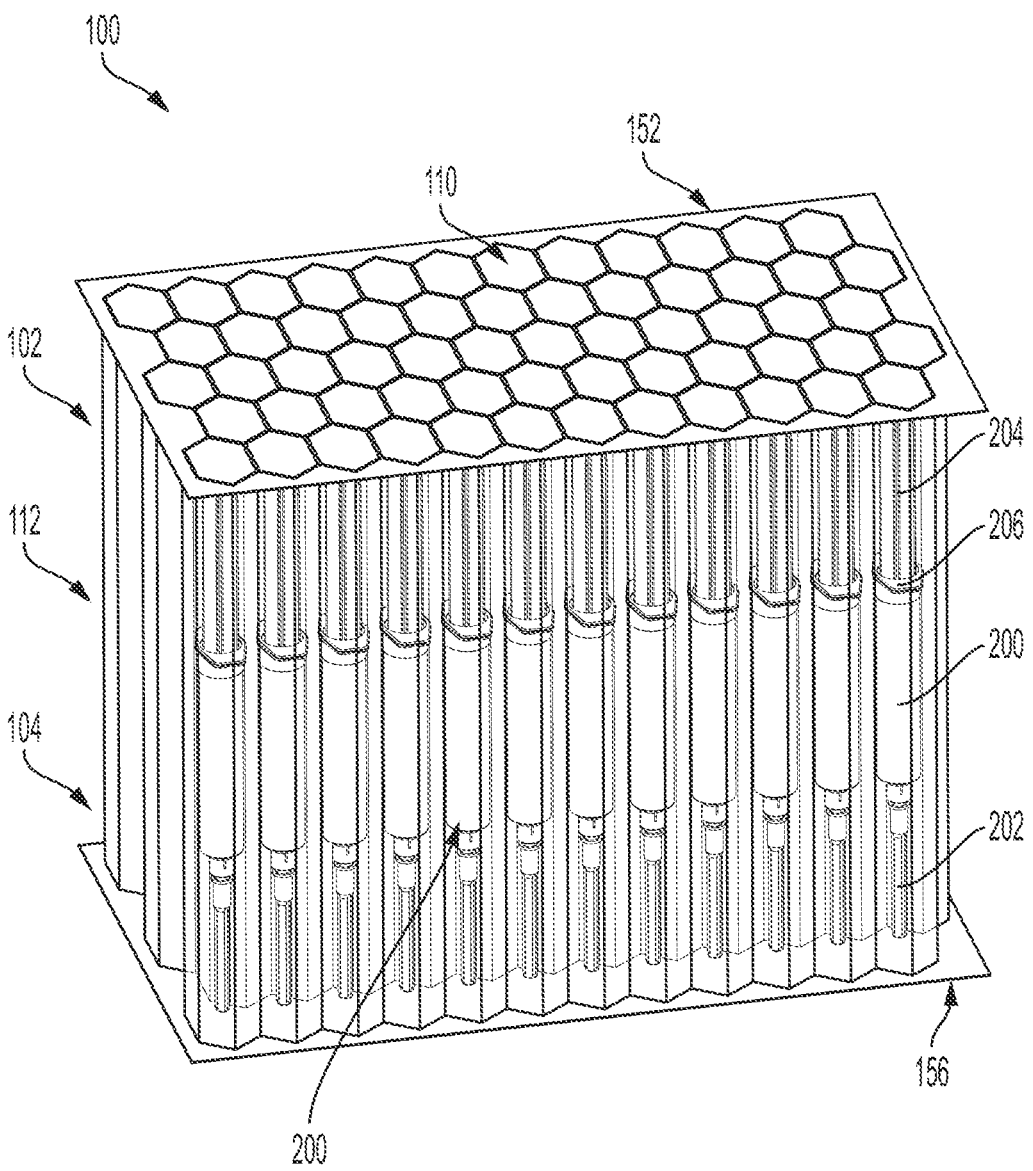
FIG. 1 is a perspective view of packaging loaded with a plurality of syringes according to an embodiment of the present disclosure.

The following description is provided to enable those skilled in the art to make and use the described aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

All numbers used in the specification and claims are to be understood as being modified in all instances by the term "about". The terms "approximately", "about", and "substantially" mean a range of plus or minus ten percent of the stated value. Further, the term "substantially equal" and like terms mean that the compared values or dimensions are within a range of plus or minus ten percent of one another.

The terms "first", "second", and the like are not intended to refer to any particular order or chronology, but refer to different conditions, properties, or elements.

As used herein with reference to an injection apparatus such as a syringe, the term "proximal" refers to an end of the apparatus farthest from the outlet, or to a direction toward the end of the apparatus farthest from the outlet. As used herein with reference to an injection apparatus such as a syringe, the term "distal" refers to an end of the device or apparatus closest to the outlet, or to a direction toward the end of the apparatus closest to the outlet.

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more of B alone; or one or more of C alone; or one or more of A and one or more of B; or one or more of A and one or more of C; or one or more of B and one or more of C; or one or more of all of A, B, and C.

Figure 2:
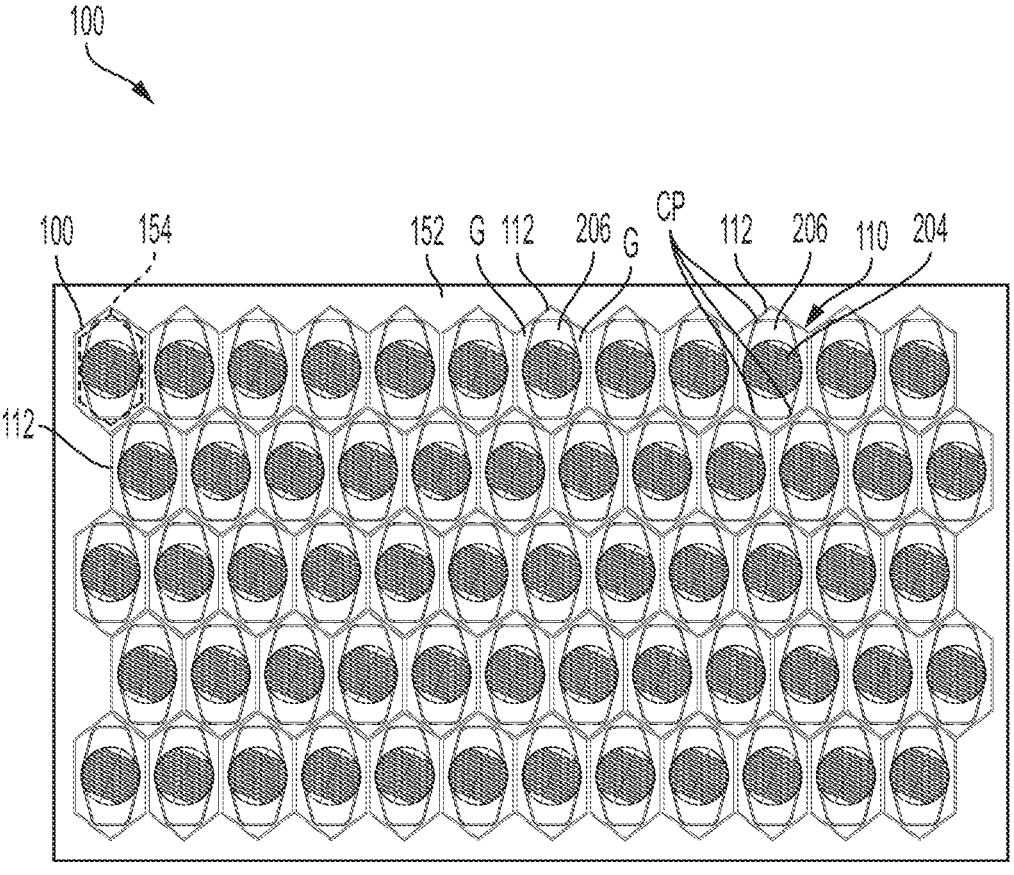
FIG. 2 is a top view of the packaging of FIG. 1 loaded with the plurality of syringes.

Referring now to FIGS. 1 and 2, an embodiment of packaging 100 for medical consumables is illustrated in a loaded configuration, in which a syringe 200 is disposed in each of a plurality of cells 110 of the packaging 100. Each of the cells 100 includes a sidewall 112 defining an elongate cavity into which the respective syringe 200 is disposed. In the orientation shown in the drawings, the syringes 200 are disposed in the cells 110 such that a needle 202 of each syringe 200 extends downward toward a base 104 of the packing, and a plunger 204 of each syringe 200 extends upward toward a top 102 of the packaging 100. All of the syringes 200 are disposed in the packaging 100 in the same orientation. In use, the packaging 100 may be rotated to any orientation, so the orientation shown in the drawings should not be construed as limiting.

Each of the cells 110 has at least one open end through which the syringe 200 is inserted and removed. For example, the top ends of the cells 110, i.e. the ends of the cells 110 adjacent the top 102 of the packaging 100, may be open. As such, the syringes 200 may be loaded and unloaded through the top 102 of the packaging 100. In the embodiments illustrated in the accompanying drawings, both ends of the cells 110 are open. In some embodiments, one end of each cell 100 may be closed, for example the ends of the cells 110 adjacent the base 104 of the packaging 100.

A top barrier film 152 may extend across the top 102 of the packaging 100 over the open ends of the cells 110 to create a seal and maintain a sterile environment within the cells 110. The top barrier film 152 may be secured to the sidewalls 112 via an adhesive or other bonding agent/process. The top barrier film 152 include a perforation 154 along the perimeter of each cell 110, allowing a portion of the top barrier film 152 associated with a particular cell 100 to be removed to access the syringe 200 housed within that cell 110. The perforation 154 may be collinear with the perimeter of the cell 110, or the perforation may be offset from the perimeter of the cell 110 toward the center of the cell 110. When the top barrier film 152 is broken along the perforation 154 associated with one cell 110 to unload the syringe 200 housed therein, the top barrier film 152 remains intact over the other cells 110 to maintain a sterile environment in all of the cells 110 not being unloaded. The perforation 154 may be particularly designed to facilitate piercing and removal by an end effector of a robotic arm (not shown). The perforation 154 is shown only in the upper left cell 110 of FIG. 2 for clarity of illustrating the other cells 110, though it is to be understood that all cells 110 have a corresponding perforation 154.

A bottom barrier film 156 may extend across the base 104 of the packaging 100 to provide a sterile seal to the bottom ends of the cells 110 in the same manner in which the top barrier film 152 seals the top ends of the cells 110. In some embodiments, the bottom barrier film 156 is substantially identical to the top barrier film 152, including perforations (not shown) analogous to the perforations 154 of the top barrier film 152. In some embodiments, where access to the syringes 200 through the bottom barrier film 156 is not intended, the bottom barrier film 156 may lack perforations and/or may be made from a thicker and/or stronger material as compared to the top barrier film 152.

With continued reference to FIGS. 1 and 2, the cross-sectional profile of the cells 110 is selected to allow zero degrees of freedom for movement of the consumables (e.g. the syringes 200) loaded in the cells 110. The sidewalls 112 of the cells 100 prevent the syringes 200 from rotation in any direction and from shifting in a direction perpendicular to longitudinal axes of the syringes 200. The top barrier film 152 and the bottom barrier film 156 prevent the syringes 200 from shifting in a direction parallel to the longitudinal axes of the syringes 200. The cross-sectional profile of the cells 110 is also selected to allow end effectors of a robotic arm (not shown) to be at least partially inserted alongside the syringes 200 so as to grasp and remove the syringes 200 from the packaging 100.

In the embodiments shown in the accompanying drawings, each of the cells 110 has a hexagonal cross-sectional profile. The hexagonal cross-section profile of each cell 110 circumscribes and interfaces with a flange 206 of the syringe 200 housed therein. In other embodiments, the cross-sectional profile of the cells 110 may be a polygon other than a hexagon to accommodate consumables of different shapes than the syringes 200. The cross-section profile defines at least one contact point CP between the sidewall 112 and the flange 206 of the syringe 200 such that the flange 206 is prohibited from rotating or shifting in a transverse direction (e.g. a direction perpendicular to the longitudinal axis of the syringe 200) due to contact with the sidewall 112. In this manner, the packaging 100 allows for zero degrees of freedom of movement of the syringes 200. The cross-section profile of the cells 110 additionally defines at least one gap G between the sidewall 112 and the flange 206 of the syringe 200 to allow an end effector of a robotic arm to be inserted between the sidewall 112 and the flange 206 to grasp the syringe 200.

As used herein, the term "zero degrees of freedom" means that each consumable (e.g. each syringe 200) is constrained such that translation and rotation in any direction are substantially prohibited. However, it may be beneficial to manufacture the cells 110 slightly oversize relative to the syringes 200 (on an order of magnitude of hundredths of an inch) such that manufacturing tolerances of the packaging 100 and/or the syringes 200 do not result in an interference fit between the syringes 200 and the sidewalls 112 of the packaging 100. As a result of the packaging 100 being slightly oversized relative to the syringes 200, the packaging 100 may allow micro-shifting of the syringes 200. Such micro-shifting poses no impediment to the functionality of the packaging 100 so long as the end effectors of the robotic arm are still able to be inserted into the gaps G between the sidewall 112 and the syringe 200. In other words, permissible micro-shifting means a rotation or translation of the syringe 200 that does not reduce the size of the gap G to a degree that the end effectors of the robotic arm are unable to pass between the sidewall 112 and the syringe 200 to reliably grasp the syringe 200. As such, the term "zero degrees of freedom", as used herein, allows for permissible micro-shifting of the syringe 200 that does not impede the ability of the robotic arm to grasp the syringe 200.

Figure 3:
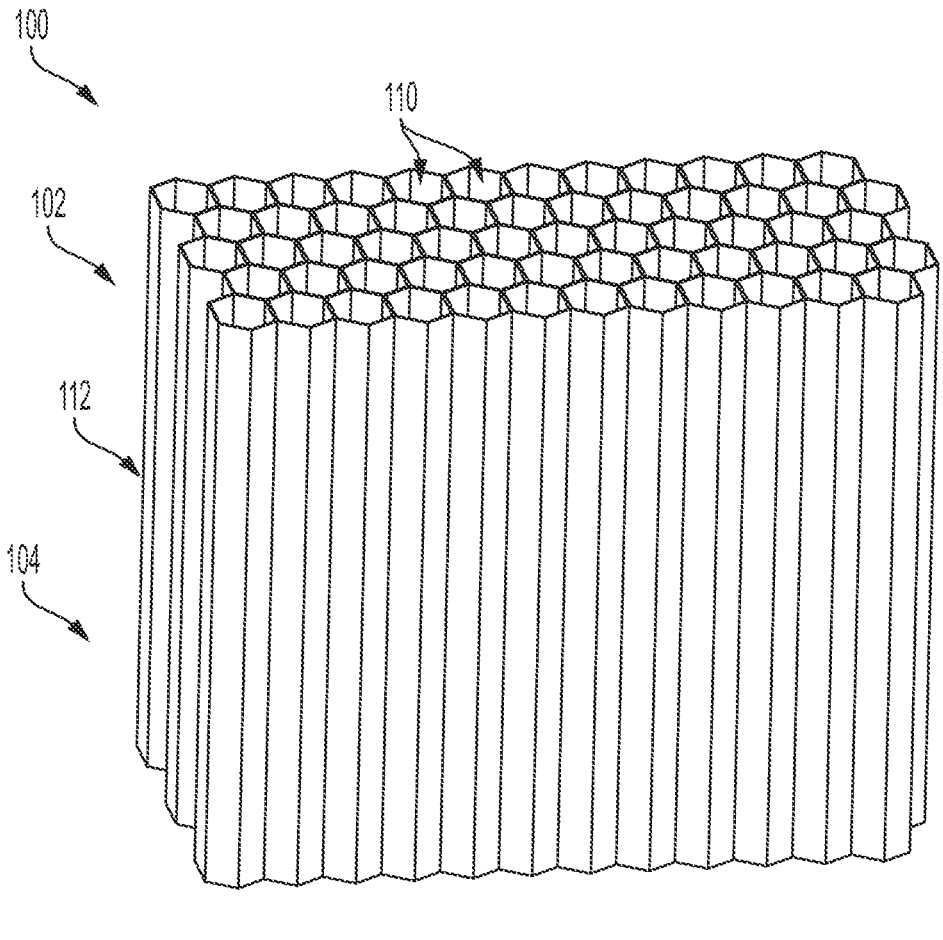
FIG. 3 is a perspective view of the packaging of FIG. 1, with the barrier film removed for clarity.
Figure 4:
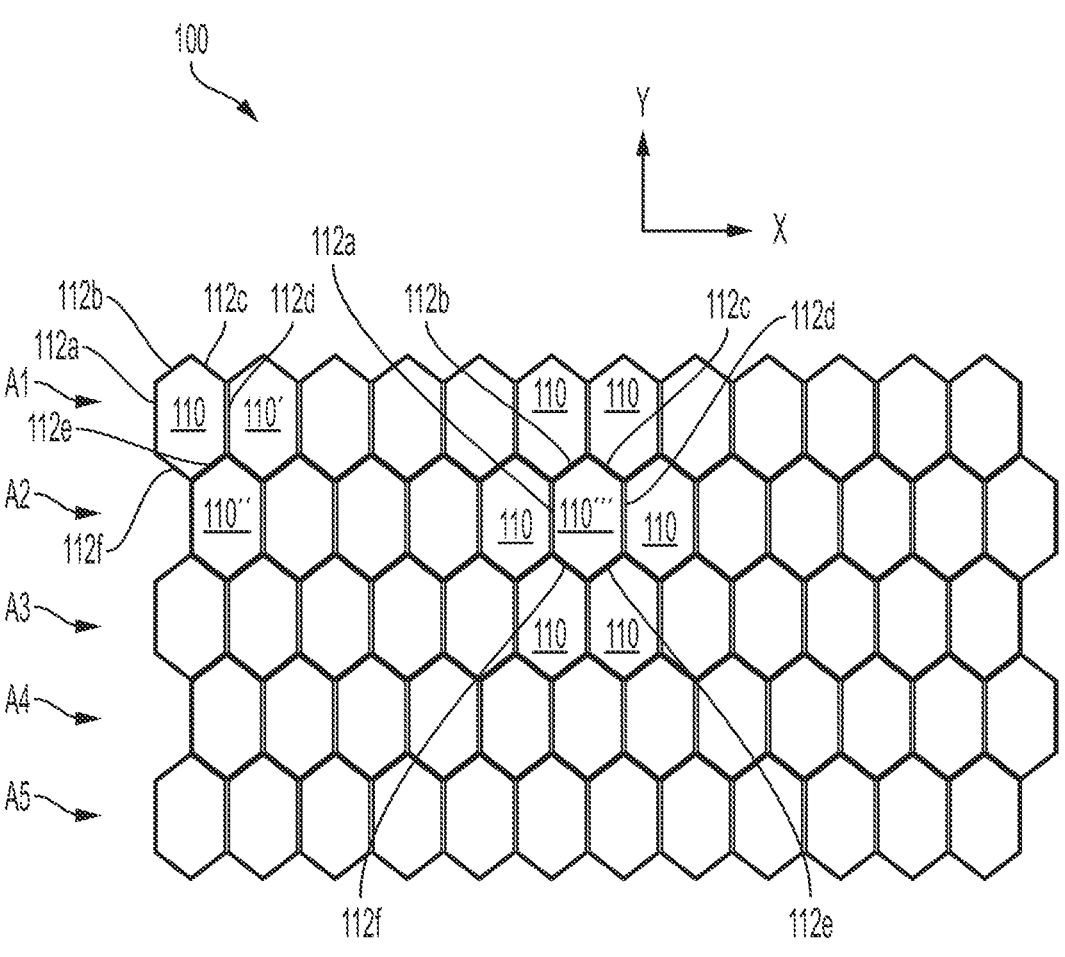
FIG. 4 is a top view of the packaging of FIG. 1, with the barrier film removed for clarity.
Figure 5:
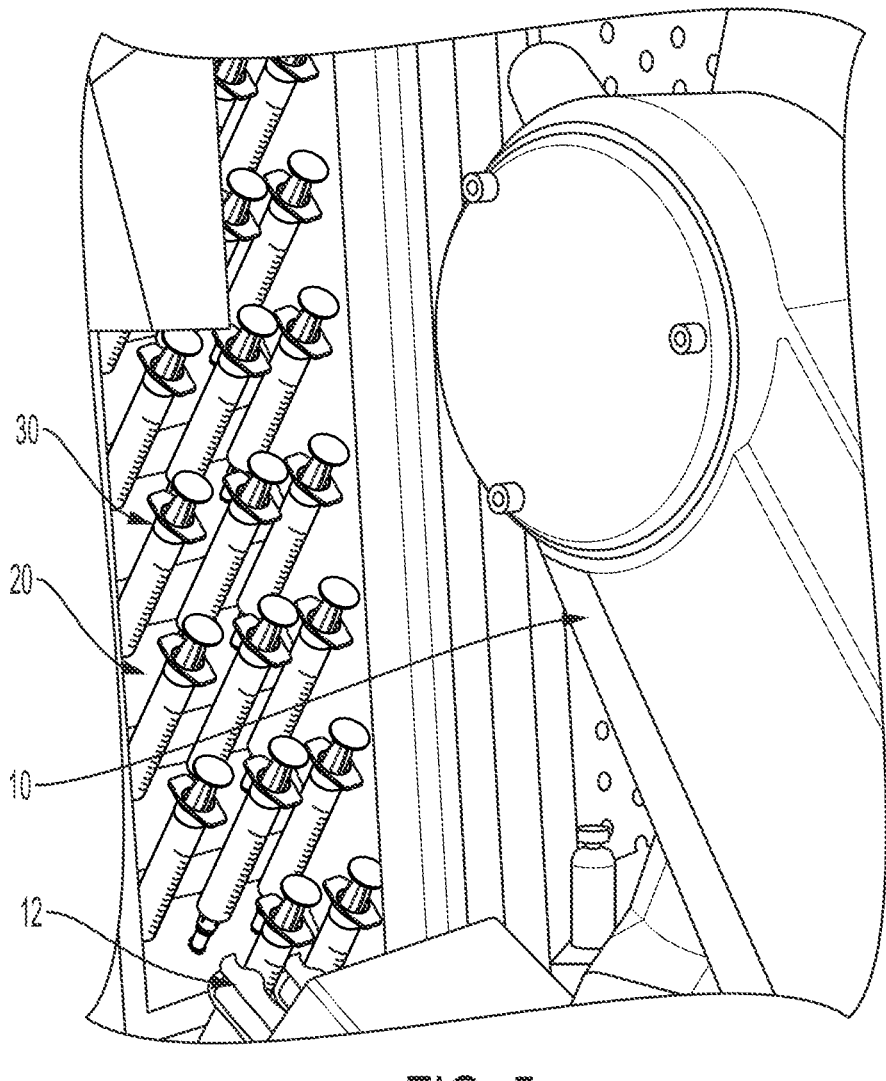
FIG. 5 is a perspective view of a prior art medical device processing robot.

With continued reference to FIGS. 1 and 2 and further reference to FIGS. 3 and 4, the cells 110 are arranged in a staggered lattice structure resembling a honeycomb to maximize the number of cells 110 per unit area. As shown in FIG. 4, the cells 110 may be arranged in a plurality of rows A1, A2, A3, A4, A5 extending in the X direction. The rows A1, A2, A3, A4, A5 are staggered such that every other row A1, A2, A3, A4, A5 is offset by half of a cell width relative to the preceding and subsequent rows. For example, the cells 110 of row A2 are offset one half cell width to the right of the cells 110 of row A1. The cells 110 of row A3 are offset one half cell width to the left of the cells 110 of row A2. Thus, the cells 110 of row A3 are in the same X positions as the cells 110 of row A1. The cells 110 of row A4 are offset one half cell width to the right of the cells 110 of row A3. Thus, the cells 110 of row A4 are in the same X positions as the cells of row A2. The cells 110 of row A5 are offset one half cell width to the left of the cells 110 of row A4. Thus, the cells 110 of row A5 are in the same X positions as the cells of row A1 and row A3. Again, it is noted that the accompanying drawings show the packaging 100 in an arbitrary orientation, and the packaging 100 could be reoriented such that the staggering is exhibited in the Y direction rather than the X direction.

Each of the rows A1, A2, A3, A4, A5 have the same number of cells 110 in the illustrated embodiments, though this not need be the case. In other embodiments, the any of the rows A1, A2, A3, A4, A5 could have different numbers of cells 110.

In the hexagonal embodiments shown in the accompanying drawings, the sidewall 112 of each cell 110 include six vertical walls forming the hexagonal profile of the cell 110. Namely, the sidewall 112 of each cell 110 includes a first wall 112a, a second wall 112b, a third wall 112c, a fourth wall 112d, a fifth wall 112e, and a sixth wall 112f. In the embodiments shown in the drawings, the first wall 112a and the fourth wall 112d are the same length. The second wall 112b, the third wall 112c, the fifth wall 112e, and the sixth wall 112f are the same length, and a different length than the first and fourth walls 112a, 112d. The cells 110 are symmetric such that the first wall 112a, the second wall 112b, and the sixth wall 112f are a mirror image of the third wall 112c, the fourth wall 112d, and the fifth wall 112e. Similarly, the cells 110 are symmetric such that the second wall 112b and the third wall 112c are a mirror image of the fifth wall 112e and the sixth wall 112f. In other embodiments, different combinations of the walls 112a-112f may be of the same or different length, or all of the walls 112a-112f may be of the same length, or all of the walls 112a-112f may be of different length. Further, the cells 110 need not be symmetric about any axis.

The walls of each cell 110 are shared between adjacent cells 110. As shown in FIG. 4, the upper left corner cell 110 of the packaging 100 borders two other cells 110', 110". The fourth wall 112d of the upper left corner cell 110 is shared with bordering cell 110', and the fifth wall 112e of the upper left corner cell 110 is shared with bordering cell 110". The first wall 112a, second wall 112b, third wall 112c, and sixth wall 112f of the upper left corner cell 110 form part of the perimeter of the packaging 100, and are not shared with any other cells 110. Cells 110 not forming a part of the perimeter of the packaging 100 are bordered by as many cells as there are walls of the sidewall 112. For example, cell 110''' of FIG. 4 is bordered by six other cells 110, with each of the first through sixth walls 112a-112f of the cell 110''' being shared with one of the bordering cells 110.

The packaging 100 may be manufactured from a variety of sterile materials. The sidewalls 112 may be made from plastic, cardboard, or pulp for example. The top barrier film 152 and the bottom barrier film 156 may be made from high barrier polymer or laminated polymer, aluminum, thermal adhesive, or the like, and in some embodiments may include a variety of such materials sandwiched together. The sidewalls 112, the top barrier film 152, and/or the bottom barrier film 156 may be made from transparent material to allow the consumables contained therein to be viewed through the packaging 100.

While the foregoing description and accompanying drawings have described the packaging 100 in the context of medical consumables, the packaging 100 of the present disclosure can readily be used in other fields in which it would be desirable to have robots remove components from packaging.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. Packaging for medical consumables, the packaging comprising:
a plurality of cells arranged in a lattice, each of the cells comprising a sidewall having a plurality of walls; and
a top barrier film covering open ends of the plurality of cells to maintain a sterile environment within the plurality of cells,
wherein the sidewalls and the top barrier film are shaped so as to constrain a consumable contained within each of the plurality of cells to zero degrees of freedom,
wherein at least one of the plurality of walls of each cell is shared with a bordering cell,
wherein the sidewall of each cell defines a gap for insertion of an end effector of a robotic arm, wherein the consumable is positionable within a cell of the plurality of cells,
wherein a flange of the consumable is positionable within the cell such that at least one edge of the flange cooperates with the sidewall to further constrain the consumable to zero degrees of freedom, and
wherein the sidewalls of each cell form a hexagonal shape that extends an entire length of the cell.

2. The packaging of claim 1, wherein the top barrier film comprises a plurality of perforations corresponding to the plurality of cells.

3. The packaging of claim 2, wherein each of the plurality of perforations is offset from a perimeter of the corresponding cell toward a center of the corresponding cell.

4. The packaging of claim 1, wherein the plurality of cells are arranged in a plurality of rows, and
wherein the cells in one of the plurality of rows are offset by one half cell width relative to the cells of a preceding row of the plurality of rows.

5. The packaging of claim 1, wherein each cell has a hexagonal cross-sectional profile.

6. The packaging of claim 1, wherein the plurality of walls comprises six walls,
wherein the length of a first wall and a fourth wall of the plurality of walls are the same length, and
wherein the length of a second wall, a third wall, a fifth wall, and a sixth wall of the plurality of walls are the same length.

7. The packaging of claim 6, wherein the second wall and the third wall of the plurality of walls are a mirror image of the fifth wall and the sixth wall of the plurality of walls.

8. The packaging of claim 1, further comprising a bottom barrier film covering base ends of the plurality of cells to maintain a sterile environment within the plurality of cells.

9. A system comprising:
a plurality of medical consumables;
packaging for the medical consumables, the packaging comprising:
a plurality of cells arranged in a lattice, each of the cells comprising a sidewall having a plurality of walls; and
a top barrier film covering open ends of the plurality of cells to maintain a sterile environment within the plurality of cells,
wherein each of the plurality of consumables is positionable in one of the plurality of cells,
wherein the sidewalls and the top barrier film are shaped so as to constrain the consumable contained within each of the plurality of cells to zero degrees of freedom,
wherein at least one of the plurality of walls of each cell is shared with a bordering cell,
wherein the sidewall of each cell defines a gap for insertion of an end effector of a robotic arm between the sidewall and the consumable disposed in each cell, and
wherein a flange of the consumable is positionable within the cell such that at least one edge of the flange cooperates with the sidewall to further constrain the consumable to zero degrees of freedom, and
wherein the sidewalls of each cell form a hexagonal shape that extends an entire length of the cell.

10. The system of claim 9, wherein each of the plurality of consumables is disposed in the packaging in the same orientation.

11. The system of claim 9, wherein the plurality of consumables comprises a plurality of syringes.

12. The system of claim 11, wherein the plurality of the syringes are disposed in the packaging such that a needle of each syringe extends toward a base of the packaging and a plunger of each syringe extends toward a top of the packaging.

13. The system of claim 9, wherein the sidewall defines at least one contact point with the consumable disposed in the cell.

14. The system of claim 9, wherein the top barrier film comprises a plurality of perforations corresponding to the plurality of cells.

15. The system of claim 14, wherein each of the plurality of perforation is offset from a perimeter of the corresponding cell toward a center of the corresponding cell.

16. The system of claim 9, wherein the plurality of cells are arranged in a plurality of rows, wherein the cells in one of the plurality of rows are offset by one half cell width relative to the cells of a preceding row of the plurality of rows.

17. The system of claim 9, wherein each cell has a hexagonal cross-sectional profile.

18. The system of claim 9, wherein the plurality of walls comprises six walls, wherein the length of a first wall and a fourth wall of the plurality of walls are the same length, and wherein the length of a second wall, a third wall, a fifth wall, and a sixth wall of the plurality of walls are the same length.

19. The system of claim 18, wherein the second wall and the third wall of the plurality of walls are a mirror image of the fifth wall and the sixth wall of the plurality of walls.

* * * * *